United States Patent [19]

Elmqvist

[11] Patent Number: 4,781,194
[45] Date of Patent: Nov. 1, 1988

[54] HEART PACEMAKER

[75] Inventor: Hakan Elmqvist, Bromma, Sweden

[73] Assignee: Siemens Aktiengesellschaft, Berlin and Munich, Fed. Rep. of Germany

[21] Appl. No.: 466,629

[22] Filed: Feb. 15, 1983

[30] Foreign Application Priority Data

Feb. 26, 1982 [DE] Fed. Rep. of Germany ....... 3207006

[51] Int. Cl.$^4$ .............................................. A61N 1/32
[52] U.S. Cl. .............................................. 128/419 PG
[58] Field of Search ................................ 128/419 PG

[56] References Cited

U.S. PATENT DOCUMENTS

| 3,942,534 | 3/1976 | Allen et al. | 128/419 PG |
| 4,108,148 | 8/1978 | Cannon, III | 128/419 PG |
| 4,181,133 | 1/1980 | Kolenik et al. | 128/419 PG |
| 4,421,116 | 12/1983 | Markowitz | 128/419 PG |

FOREIGN PATENT DOCUMENTS 0016574 3/1983 European Pat. Off. .
2236434 4/1979 Fed. Rep. of Germany .
2939197 4/1981 Fed. Rep. of Germany .

OTHER PUBLICATIONS

Siemens Elema Brochure ME 372/5406, 1979, "The Multiprogrammable Pulse Generator 668".

Primary Examiner—William E. Kamm
Attorney, Agent, or Firm—Hill, Van Santen, Steadman & Simpson

[57] ABSTRACT

A heart pacemaker has a controllable time delay element for setting the time between atrial and ventricular activity (AV time). For terminating tachycardia as quickly as possible with such a heart pacemaker, a detector for detecting tachycardia is provided with the time delay element being driven by means of the detector such that the AV time is altered upon the occurrence of tachycardia. The change in the AV time is selected such that the new AV time is an optimum for terminating tachycardia. After a preselected time, the time delay element returns to the original AV time.

14 Claims, 1 Drawing Sheet

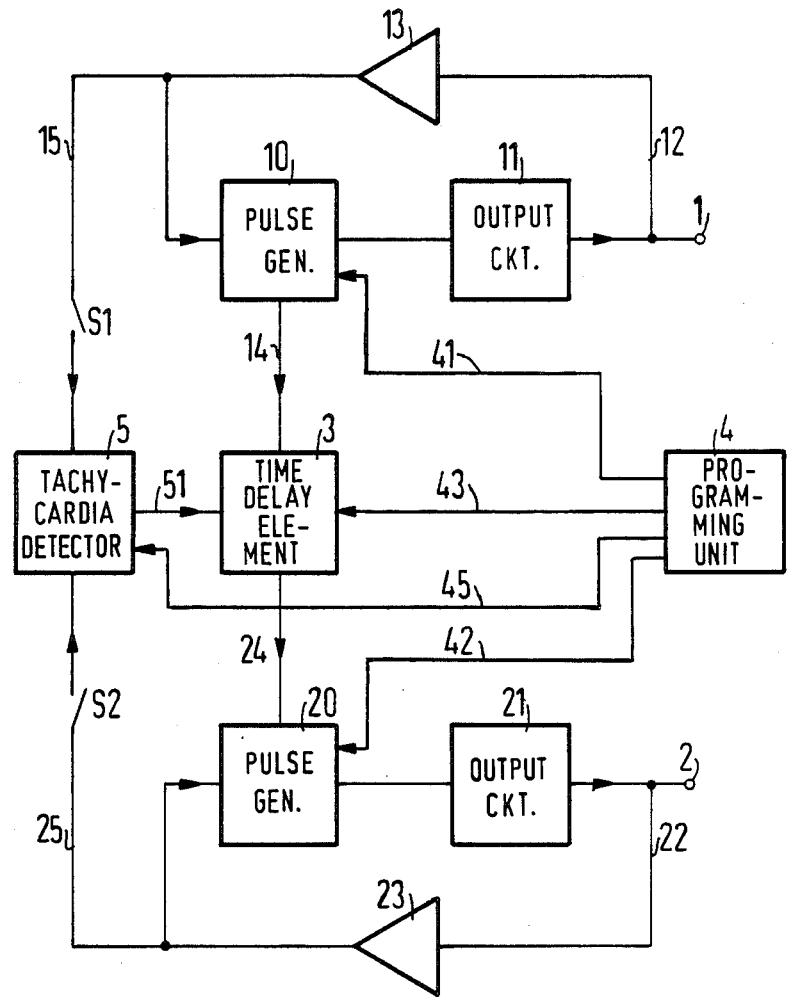

HEART PACEMAKER

BACKGROUND OF THE INVENTION

Field of the Invention

The present invention relates to heart pacemakers, and in particular to such a heart pacemaker hvaing a time delay element therein for setting the time between atrial and ventricular activity (AV time).

Description of the Prior Art

Atrioventricular-sequential (or AV-sequential) heart pacemakers generally are those types of heart pacemakers which provide a stimulation pulse to the ventricle controlled by an atrial signal, or provide a stimulation pulse to the ventricle and the atrium controlled by an atrial signal, as well as pacemakers which provide a stimulation pulse to both the atrial and the ventricle and are controlled by signals from both chambers. Such a heart pacemaker is described, for example, in U.S. Pat. No. 4,108,148. It is known that the hemodynamically effective PQ time can be matched to the heartbeat frequency by the use of a time delay element.

SUMMARY OF THE INVENTION

It is an object of the present invention to provide an heart pacemaker for preventing or at least quickly terminating treatable tachycardia such as, for example, re-entry tachycardia.

The above object is inventively achieved in an heart pacemaker having a detector for detecting an existing tachycardia, or warning of such an event before the occurrence thereof, which generates an output signal which is supplied to a time delay element which effects a change of the AV time, the change being selected such that the new AV time is an optimum for preventing or terminating the tachycardia. After the elapse of a predetermined time, the time delay element returns to the original AV time.

Heart pacemakers are known by means of which tachycardia can be terminated such as, for example, those described in British patent No. 7,907,998 and U.S. Pat. No. 3,942,534. In those pacemakers, a special detector is provided for identifying tachycardia. Upon the occurrence of tachycardia, additional stimulation pulses are emitted to the heart. In order to terminate tachycardia, the heart must be stimulated at a proper point in time, and thus be transferred into a refractory phase, so that the cycle causing the tachycardia is neutralized. For the purpose, the pacemaker described in U.S. Pat. No. 3,942,534 continuously changes the chronological spacing between such stimulation pulses after each heart cycle, either abbreviating or extending the spacing. Given a sufficiently large number of stimulation pulses, the proper time spacing relative to the heart activity should in theory be reached in order to terminate tachycardia. It is known from the above-cited British patent to utilize the heart activity following a stimulation pulse for targeting the time control, i.e., the selected spacing, for the next stimulation pulse.

AV sequential heart pacemakers are also known which are utilized for treating tachycardia, however, pacemakers of this type always utilize a fixed delay time, independently of whether tachycardia is present or not. This frequently results in the patient's having such pacemakers suffering from hemodynamic complaints.

The heart pacemaker discosed and claimed herein terminates tachycardia in a relatively simple manner by the stimulation in the ventricle being undertaken with a specific time delay relative to the event in the atrium. The reverse is also possible, however, i.e., deriving control signals from the ventricle in order to undertake stimulation in the atrium. The heart pacemaker disclosed and claimed herein makes use of a variable delay time between the heart activites in one chamber and the stimulation pulses supplied to the other chamber. This is achieved by means of a detector for detecting tachycardia which supplies an output signal to the time delay element for controlling the delay time. In the simplest case, the delay time upon the occurrence of tachycardia may change to a single predetermined and unchanging value.

In order to expand the uses for such a heart pacemaker, however, the detector input may be selectively connectable to the atrial or the ventricular electrode. Moreover, the time delay element may be constructed such that, after being driven by the occurrence of a tachycardia signal from the detector and subsequently varying the delay time, the delay element returns to the original delay time after a fixed predetermined time. Should be tachycardia still exist, the detector will again drive the delay element to again vary the delay time.

In a further embodiment of the invention the delay time returns to the original value only after tachycardia is terminated. The altered output signal of the detector is employed after termination of tachycardia for renewed drive of the time delay element.

As described above, the delay time given the presence of tachycardia may be permanently selected, however, it is also possible to alter the delay time according to a predetermined pattern, for example, to abbreviate or expand the delay time by a selected amount after each heart cycle. Tachycardia may be terminated particularly rapidly by the use of the present invention in combination with the recognition that the change of the AV time is a function of the electro-physiological reaction of the heart to earlier stimulation pulses.

Both permanently selected delay times or delay times variable according to a specific pattern can be set by the format of the time delay element, or may be set by a wireless external programming unit.

DESCRIPTION OF THE DRAWING

The single FIGURE is a schematic block diagram of a heart pacemaker constructed in accordance with the principles of the present invention.

DESCRIPTION OF THE PREFERRED EMBODIMENTS

As shown in the drawings, a heart pacemaker constructed in accordance with the principles of the present invention has two terminals 1 and 2 which are respectively connected to heart electrodes. The electrodes connected to the terminal 1 supplies pulses to the atrium and the electrode connected to the terminal 2 supplies pulses to the ventricle. The pulses for both terminals are generated in a known manner by respective pulse generators 10 and 20 which are connected to respective output circuits 11 and 21 for generating the stimulation pulses. The electrodes connected to the terminals 1 and 2 simultaneously function for sensing heart activity. The signals received in such a manner are supplied to the pulse generators 10 and 20 as control signals via respective lines 12 and 22 and respective amplifiers 13 and 23.

The heart pacemaker further includes a time delay element 3 which controls the delay time between the heart activity in one chamber and the supply of a stimulation pulse to the other chamber. In the embodiment shown in the drawing, the time delay element 3 is driven by the pulse generator 10 via a line 14. This drive may, for example, occur when the pulse generator 10 emits a stimulation pulse to the atrium or when the corresponding electrode 1 indicates a spontaneous activity in the atrium. After a specific adjustable time delay, the time delay element 3 emits an output signal to the pulse generator 20 via a line 24. Only after receipt of such a signal is a stimulation pulse generated by the pulse generator 20 for supply to the ventricular electrode via the terminal 2.

The reverse case is also possible without departing from the inventive concept disclosed herein, that is, the pulse generator 20 may emit a control signal to the time delay element 3 which in turn triggers the generation of pulses by the pulse generator 10. In that instance, the direction of the arrows associated with the lines 14 and 24 would be reversed.

As indicated by dashed lines 41, 42 and 43, a number of function parameters of the pulse generator 10, the pulse generator 20 and the time delay element 3 may be altered by means of an external programming unit 4. Such a programming unit may be of the type described, for example, in Siemens Elema Brochure ME 372/5406, 1979. The manner by which such programming is undertaken is known to those skilled in the art as described, for example, in German AS No. 2,236,434 or German OS No. 2,939,197.

The heart signals detected by the electrodes 1 or 2 and amplified by the amplifiers 13 or 23 are supplied to a tachycardia detector 5 via respective lines 15 and 25 and respective switches S1 and S2. On the basis of the state of the switches S1 and S2, the tachycardia detector 5 can selectively analyze the atrial signals or the ventricular signals. A tachycardia detector which is suitable for use as the detector 5 in the present invention is described, for example, in U.S. Pat. No. 3,942,534. The output signal of the tachycardia detector 5 is forwarded to the time delay element 3 as an additional control signal over a line 51. As indicated by the dashed line 45, however, function parameters of the tachnycardia detector 5 such as, for example, its sensitivity, may also be varied by means of the external programming unit 4 disposed outside the heart pacemaker.

The manner of operation of the heart pacemaker shown in the drawing is as follows. As long as the tachycardia detector 5 does not indicate the presence of tachycardia, the circuit functions as a known AV-sequential heart pacemaker. As long as no changes in the parameters are undertaken by the external programming unit 4, the time delay of the time delay element 3 is fixed. Under certain conditions, however, the delay time may change depending upon whether heart activities in the atrium are spontaneous or are induced by a stimulation pulse.

When tachycardia or an ectopic heartbeat (induced at the wrong location of the heart and generally preceding the beginning of tachycardia) is registered, the tachycardia detector 5 generates an output signal causing a change in the time delay (AV time) of the time delay element 3. The delay time selected in such a case may, as is known, be a single abbreviated delay time or may be a delay time variable according to a predetermined pattern. When the tachycardia has been terminated, the output signal of the detector 5 returns to its original value and the time delay of the time delay element 3 also returns to its initial value.

The advantage of the heart pacemaker described above lies primarily in the fact that the preliminary warning of tachycardia can be sensed and countermeasures may be directly undertaken so that tachycardia does not even occur. When, for example, such an ectopic heartbeat is detected by the tachycardia detector 5, which without counter-measures would lead to a cyclical activation atrium-ventricle-atrium, that is, to tachycardia, a stimulation pulse can be emitted to the ventricle with a targeted short delay time relative to the ectopic heart activity, the stimulation pulse placing the ventricle in a refractory phase thus making it unreceptive for the activation signal arriving from the atrium. Further activation is thus blocked.

Another advantage of the heart pacemaker disclosed and claimed herein is that, as a result of detecting the activity in one chamber and controlling the time delay as a function of this activity, the stimulation pulses provided for terminating tachycardia can be better fixed in terms of time behavior, so that the changes for a fast and effective termination of tachycardia are further enhanced.

Although modifications and changes may be suggested by those skilled in the art it is the intention of the inventor to embody within the patent warranged hereon all changes and modifications as reasonably and properly come within the scope of his contribution to the art.

I claim as my invention:

1. A heart pacemaker comprising:
   atrial terminal means and ventricular terminal means for respective connection to the atrium and ventricle of a heart;
   ventricular pulse generating means connected to said ventricular terminal means for delivering stimulating pulses to said ventricle;
   atrial sensing means connected to said atrial terminal means for sensing contractions of said atrium;
   a tachycardia detector having an input connected to said atrial sensing means for detecting tachycardia; and
   a programmable delay element having an input connected to said atrial sensing means and having an output connected to said ventricular pulse generating means for normally triggering said ventricular pulse generating means after a first time delay following an atrial contraction (AV time), said programmable delay element having another input connected to the output of said tachycardia detector for triggering said ventricular pulse generator upon receipt of a signal from said tachycardia detector after a selected programmed second time delay for terminating said tachycardia, said programmable time delay including means for subsequently returning to said first delay time if said second delay time occurs.

2. The heart pacemaker of claim 1 wherein said means in said time delay element for returning to said first delay time includes means for returning to said first delay time after a programmed predetermined time.

3. The heart pacemaker of claim 1 wherein said means in said time delay element for returning to said first delay time includes means for returning to said first delay time after termination of tachycardia.

4. The heart pacemaker of claim 1 wherein said time delay element includes means for varying said second delay time.

5. The heart pacemaker of claim 4 further comprising an external programming unit for programming said time delay element for varying said second delay time for selecting a programmed change in said second delay time which is optimum for terminating said tachycardia.

6. The heart pacemaker of claim 4 wherein said means in said time delay element for varying said second delay time includes means for varying said second delay time after each heart cycle by a different programmed predetermined amount.

7. The heart pacemaker of claim 4 wherein said means in said time delay element for varying said second delay time includes means for varying said second delay time as a function of the electro-physiological reaction of the heart to an earlier stimulation pulse.

8. A heart pacemaker comprising:
   atrial terminal means and ventricular terminal means for respective connection to the atrium and ventricle of a heart;
   ventricular pulse generating means connected to said ventricular terminal means for delivering stimulating pulses to said ventricle;
   atrial sensing means connected to said atrial terminal means for sensing contractions of said atrium;
   a ventricular sensing means connected to said ventricular terminal means for sensing contractions of said atrium;
   a tachycardia detector for detecting tachycardia;
   switch means selectively connecting one of said atrium or ventricular sensing means to an input of said tachycardia detector; and
   a programmable delay element having an input connected to said atrial sensing means and having an output connected to said ventricular pulse generating means for normally triggering said ventricular pulse generating means after a first time delay following an atrial contraction (AV time), said programmable delay element having another input connected to the output of said tachycardia detector for triggering said ventricular pulse generator upon receipt of a signal from said tachycardia detector after a selected programmed second time delay for terminating said tachycardia, said programmable time delay including means for subsequently returning to said first delay time if said second delay occurs.

9. The heart pacemaker of claim 8 wherein said means in said time delay element for returning to said first delay time includes means for returning to said first delay time after a predetermined programmed time.

10. The heart pacemaker of claim 8 wherein said time delay element includes means for varying said second delay time.

11. The heart pacemaker of claim 10 further comprising an external programming unit for controlling said time delay element for selecting a change in said second delay time which is optimum for terminating said tachycardia.

12. The heart pacemaker of claim 10 wherein said means in said time delay element for varying said second delay time includes means for varying said second delay time after each heart cycle by a different programmed predetermined amount.

13. The heart pacemaker of claim 10 wherein said means in said time delay element for varying said second delay time includes means for varying said second delay time as a function of the electro-physiological reaction of the heart to an earlier stimulation pulse.

14. The heart pacemaker of claim 8 wherein said means in said time delay element for returning to said first delay time includes means for returning to said first delay time after termination of tachycardia.

* * * * *